US009943316B2

United States Patent
Kornowski et al.

(10) Patent No.: US 9,943,316 B2
(45) Date of Patent: Apr. 17, 2018

(54) RADIAL ARTERY DEVICE

(71) Applicant: MOR RESEARCH APPLICATION LTD., Tel-Aviv (IL)

(72) Inventors: Ran Kornowski, Ramat-HaSharon (IL); Hana Vaknin Assa, Ramat-Gan (IL)

(73) Assignee: MOR RESEARCH APPLICATION LTD., Tel-Aviv (IL)

( * ) Notice: Subject to any disclaimer, the term of this patent is extended or adjusted under 35 U.S.C. 154(b) by 359 days.

(21) Appl. No.: 14/421,160

(22) PCT Filed: Aug. 12, 2013

(86) PCT No.: PCT/IL2013/050685
§ 371 (c)(1),
(2) Date: Feb. 12, 2015

(87) PCT Pub. No.: WO2014/027347
PCT Pub. Date: Feb. 20, 2014

(65) Prior Publication Data
US 2015/0201948 A1  Jul. 23, 2015

Related U.S. Application Data

(60) Provisional application No. 61/682,352, filed on Aug. 13, 2012.

(51) Int. Cl.
*A61B 17/00* (2006.01)
*A61B 17/132* (2006.01)
(Continued)

(52) U.S. Cl.
CPC ...... *A61B 17/1325* (2013.01); *A61B 5/02042* (2013.01); *A61B 5/0261* (2013.01);
(Continued)

(58) Field of Classification Search
CPC ............ A61B 17/1325; A61B 17/1322; A61B 17/135; A61B 17/1355; A61B 5/02042
See application file for complete search history.

(56) References Cited

U.S. PATENT DOCUMENTS 4,509,528 A  4/1985  Sahota
5,197,972 A  3/1993  Hakki
(Continued)

FOREIGN PATENT DOCUMENTS

DE  102007054494 A1  5/2009
JP  2003135472 A  5/2003
(Continued)

OTHER PUBLICATIONS

Pancholy SB et al. "Prophet Study", Catheterization and Cardiovascular Interventions, Sep. 1, 2008, pp. 335-340 vol. 72, Issue 3, Published on behalf of the Society for Cardiovascular Angiography and Interventions, (6 pages).
(Continued)

*Primary Examiner* — Jonathan Miles
(74) *Attorney, Agent, or Firm* — Roach Brown McCarthy & Gruber, P.C.; Kevin D. McCarthy

(57) ABSTRACT

According to an aspect of some embodiments of the present invention there is provided a vessel pressure control device configured for selectively applying pressure to a radial artery, the device comprising: a sensor configured to sense one or more parameters associated with blood flow through a portion of the radial artery; a pressure application element adapted to apply variable amounts of pressure to the portion of the radial artery; and a controller configured to apply logic and generate a signal to control the pressure application element in response to the one or more measured parameters, the signal controlling the pressure application element to modify or maintain the applied pressure so that at least some blood flow is maintained through the radial artery
(Continued)

portion in an amount sufficient to reduce or prevent radial artery occlusion, and so that the applied pressure is sufficient to prevent bleeding from the portion.

13 Claims, 6 Drawing Sheets

(51) Int. Cl.
    *A61B 5/02*         (2006.01)
    *A61B 5/026*      (2006.01)
    *A61B 17/135*     (2006.01)
    *A61B 5/00*         (2006.01)
    *A61B 90/00*      (2016.01)

(52) U.S. Cl.
    CPC ........ *A61B 5/4836* (2013.01); *A61B 17/1355* (2013.01); *A61B 90/06* (2016.02); *A61B 2090/065* (2016.02)

(56) References Cited

U.S. PATENT DOCUMENTS

| | | | |
|---|---|---|---|
| 5,307,811 A * | 5/1994 | Sigwart | A61B 17/132 600/481 |
| 5,643,315 A * | 7/1997 | Daneshvar | A61B 17/135 606/201 |
| 6,572,636 B1 | 6/2003 | Hagen et al. | |
| 7,486,131 B2 | 2/2009 | Murofushi et al. | |
| 2010/0191277 A1 | 7/2010 | McEwen et al. | |
| 2012/0053617 A1* | 3/2012 | Benz | A61B 17/1325 606/203 |

FOREIGN PATENT DOCUMENTS

| | | |
|---|---|---|
| JP | 2008188351 A | 8/2008 |
| JP | 2010173346 A | 8/2010 |
| JP | 2011521678 A | 7/2011 |
| WO | 9846144 A1 | 10/1998 |
| WO | 2009012594 A1 | 1/2009 |
| WO | 2009117447 A1 | 9/2009 |

OTHER PUBLICATIONS

Dancholy SB et al. "Impact of two different hemostatic devices on radial artery outcomes after transradial catheterization", J Invasive Cardiol. Mar. 2009; vol. 21(3):101-104. (5 pages).

Barbeau GR et al. "Evaluation of the ulnopalmar arterial arches with pulse oximetry and plethysmography: comparison with the Allen's test in 1010 patients". American Heart Journal. Mar. 2004; vol. 147(3): pp. 489-493, Quebec, Canada (5 pages).

* cited by examiner

RADIAL ARTERY DEVICE

FIELD AND BACKGROUND OF THE INVENTION

The present invention, in some embodiments thereof, relates to a device for applying pressure to a bleeding vessel, more particularly, but not exclusively, to a device for applying pressure to the radial artery to prevent bleeding while allowing at least some blood flow therethrough.

Pancholy S B et al. "PROPHET Study", Catheterization and Cardiovascular Interventions, Vol. 72, Issue 3, pages 335-340, 1 Sep. 2008, disclose "Patent hemostasis is highly effective in reducing radial artery occlusion after radial access and guided compression should be performed to maintain radial artery patency at the time of hemostasis, to prevent future radial artery occlusion."

Pancholy S B et al. "Impact of two different hemostatic devices on radial artery outcomes after transradial catheterization", J Invasive Cardiol. 2009 Mar; 21(3):101-4. Disclose "A significant reduction in radial artery occlusion was noted with hemostasis using the TR Band compared to the HemoBand, without compromising hemostatic efficacy."

U.S. Pat. No. 4,509,528 discloses "A hemostat for restricting blood flow through a blood vessel for assisting hemostasis. An ultrasonic sensor is mounted with a pressure pad to sense rate of blood flow through the vessel when pressure is applied to obtain minimum bleeding with maximum flow through the vessel, without need for continual observation."

U.S. Pat. No. 5,197,972 discloses "An arterial manometric dressing includes a pressure applying assembly having a pressure pad at a lower end thereof. A Doppler probe for determining blood flow in an artery forms part of the pressure applying assembly . . . ."

US Patent Application No. 2010/0191277 discloses "A system for controlling blood flow through a zone of a patient limb . . . ."

PCT publication NO. WO 98/46144 discloses "A hemostasis device and method is provided for closing wounds by the application of pressure."

Additional background art includes:
DE 102007054494 A1
U.S. Pat. No. 5,307,811
U.S. Pat. No. 6,572,636
U.S. Pat. No. 7,486,131
WO 2009/117447

Barbeau G R et al. Evaluation of the ulnopalmar arterial arches with pulse oximetry and plethysmography: comparison with the Allen's test in 1010 patients. Am Heart J. 2004 Mar; 147(3):489-93.

SUMMARY OF THE INVENTION

An aspect of some embodiments of the invention relates to a device for selectively applying enough pressure to prevent a radial artery from bleeding while allowing a predetermined amount of blood to flow through the radial artery.

According to an aspect of some embodiments of the present invention there is provided a vessel pressure control device configured for selectively applying pressure to a radial artery, the device comprising:
a sensor configured to sense one or more parameters associated with blood flow through a portion of the radial artery;
a pressure application element adapted to apply variable amounts of pressure to the portion of the radial artery; and
a controller configured to apply logic and generate a signal to control the pressure application element in response to the one or more measured parameters, the signal controlling the pressure application element to modify or maintain the applied pressure so that at least some blood flow is maintained through the radial artery portion in an amount sufficient to reduce or prevent radial artery occlusion, and so that the applied pressure is sufficient to prevent bleeding from the portion.

According to some embodiments of the invention, the sensor comprises a Doppler ultrasound sensor positioned and adapted to measure a blood flow rate through the radial artery portion.

According to some embodiments of the invention, the sensor is adapted to sense the one or more parameters on a finger.

According to some embodiments of the invention, the device further comprises a memory in electrical communication with the controller, the memory storing one or more value thresholds and/or ranges for monitoring the sensed parameter.

According to some embodiments of the invention, the device further comprises a memory in electrical communication with the controller, the memory storing data associating the one or more parameters with an applied pressure.

According to some embodiments of the invention, the device further comprises a communication element adapted to transmit signals associated with the one or more parameters.

According to some embodiments of the invention, the device further comprises a bleeding sensor adapted to detect bleeding from the radial artery portion and send a bleeding signal associated with the bleeding to the controller, the controller adapted to send the signal to the pressure application element to increase the applied pressure in response to the bleeding signal.

According to some embodiments of the invention, the device further comprises an output element adapted to provide output associated with the one or more parameters.

According to some embodiments of the invention, the sensor is positioned within the pressure application element.

According to some embodiments of the invention, the sensor is adapted to measure a direction of blood flow through the radial artery portion.

According to some embodiments of the invention, the pressure application element has a pressure applying surface of about 25 $mm^2$ to about 400 $mm^2$.

According to some embodiments of the invention, the device further comprises a strap sized to fit around a wrist.

According to some embodiments of the invention, the sensor is adapted to sense the one or more parameters at a depth of no more than about 10 mm.

According to an aspect of some embodiments of the present invention there is provided a device adapted for measuring blood flow through a portion of a radial artery, the device comprising:
a sensor adapted to sense one or more parameters associated with an amount of blood flow through the portion, the sensor is adapted to sense the one or more parameters at a depth of no more than about 10 mm; and
an output interface electrically coupled to the sensor, the output interface configured to provide output according to one or more predetermined thresholds and/or ranges of the one or more parameters.

According to some embodiments of the invention, the sensor comprises a Doppler ultrasound sensor.

According to some embodiments of the invention, the output is further configured to output a direction of the blood flow.

According to some embodiments of the invention, the sensor comprises a sensing region sized to receive echoes from a portion of the radial artery without sensing other vessels.

According to some embodiments of the invention, the device is sized and shaped to be compatible with other radial artery closure devices.

According to some embodiments of the invention, the output comprises a first output type if the one or more parameters fall within the range and/or the threshold, and a second output type if the one or more parameters do not fall within the range and/or the threshold.

According to some embodiments of the invention, a surface of the device comprises an adhesive on a contact surface thereof for mechanically coupling the device to skin.

According to an aspect of some embodiments of the present invention there is provided a method of controlled closure of a portion of a radial artery comprising:
applying pressure to the radial artery portion in an amount to stop bleeding from the radial artery portion; and
maintaining or adjusting the applied pressure, so that enough blood flows through the radial artery portion to prevent or reduce radial artery occlusion, while the stopped bleeding is maintained.

According to some embodiments of the invention, the method further comprises monitoring one or more parameters associated with blood flow through the radial artery portion, and wherein the maintaining or adjusting comprises maintaining or adjusting according to the monitoring.

According to some embodiments of the invention, applying pressure to the radial artery portion comprises applying about 60-100 mmHg to the radial artery portion.

According to some embodiments of the invention, applying pressure to the radial artery portion comprises applying pressure so that a rate of blood flow through the radial artery portion is reduced to about 10-40 ml/min.

According to some embodiments of the invention, applying comprises applying pressure so that the blood flow is inadequate to oxygenate a hand without collateral blood flow from an ulnar artery.

According to some embodiments of the invention, applying comprises applying pressure to the radial artery portion without compressing a radial nerve to cause symptoms.

According to some embodiments of the invention, the method further comprises monitoring a direction of the blood flow through the radial artery portion.

According to some embodiments of the invention, the applying comprises applying pressure to maintain a blood flow of at least 50% of a baseline.

According to some embodiments of the invention, the method further comprises monitoring the blood flow proximal to a branch point of the radial artery and/or to an arterial arch.

According to some embodiments of the invention, applying comprises applying pressure to prevent transmission of pulses through the radial artery portion.

According to some embodiments of the invention, adjusting comprises reducing the applied pressure in response to a vessel spasm.

According to some embodiments of the invention, applying comprises applying according to a protocol.

According to some embodiments of the invention, the method further comprises monitoring oxygenation of tissues of a hand containing the radial artery portion.

According to some embodiments of the invention, the method further comprises performing one or more measurements to obtain calibration data.

According to some embodiments of the invention, the method further comprises comparing the blood flow to the calibration data.

According to some embodiments of the invention, applying pressure comprises applying enough pressure so that a cross sectional area of the radial artery portion is reduced by about 50-90%.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
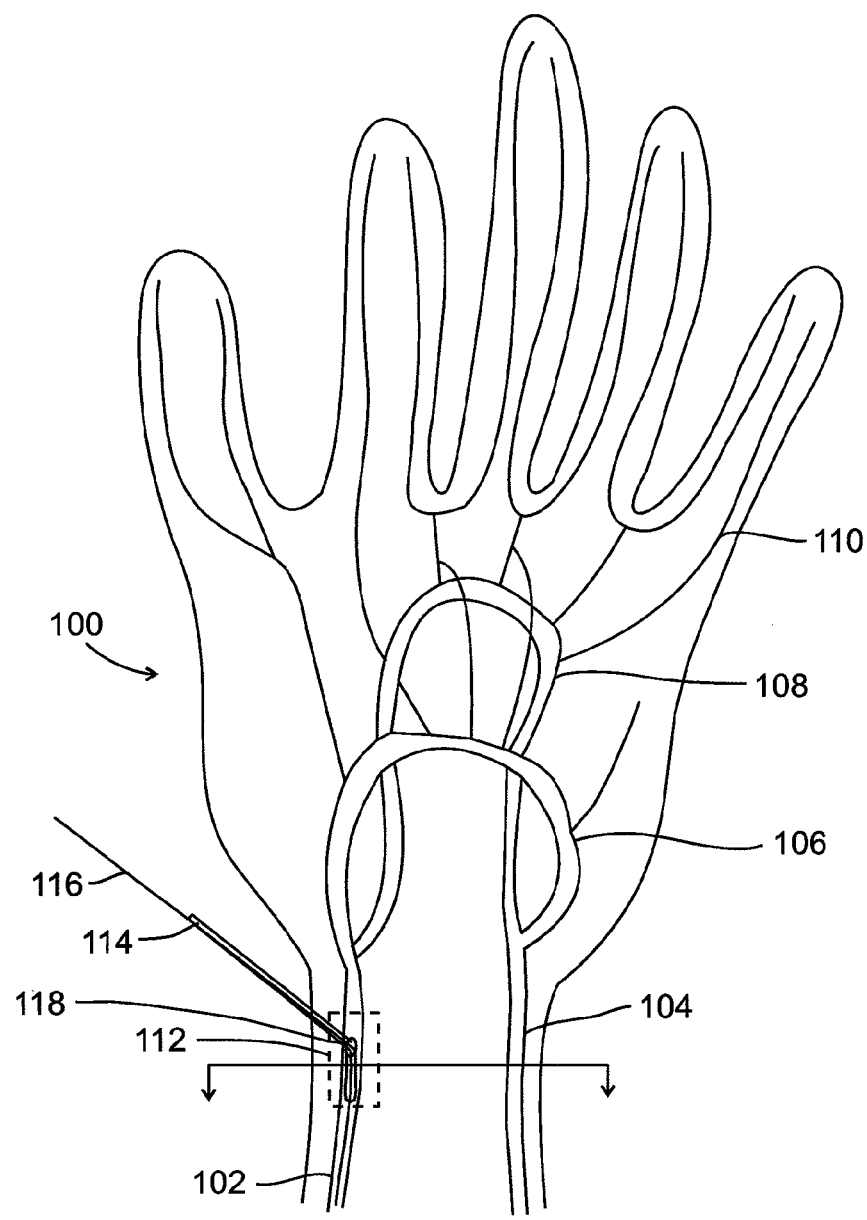
FIG. 1 is a schematic diagram of the hand, to help understand an exemplary embodiment of the invention.

The present invention, in some embodiments thereof, relates to a device for applying pressure to a bleeding vessel, more particularly, but not exclusively, to a device for applying pressure to the radial artery to prevent bleeding while allowing at least some blood flow therethrough.

An aspect of some embodiments of the invention relates to a device for controlling the application of enough pressure to prevent a radial artery from bleeding from an access site, while allowing a predetermined amount of blood to flow through the radial artery access site. In an exemplary embodiment of the invention, the predetermined amount of blood is sufficient to prevent or reduce the occlusion rate of the radial artery. The risk of occlusion (e.g., using statistical analysis) is reduced, for example, by at least 30%, at least 50%, at least 70%, at least 90%, or other smaller, intermediate or larger percentages.

As used herein, the term/phrase 'radial artery occlusion' means an occlusion of the radial artery without the application of an external pressure, Radial artery occlusion is different than a narrowing of the lumen by the external application of pressure. Without being bound to theory, radial artery occlusion is a physiological process. Radial artery occlusion is a possible complication of transradial access. Radial artery occlusion may be problematic by precluding future transradial access. Radial artery occlusion may be chronic, long term and/or permanent. Radial artery occlusion may develop a period of time after the radial artery access procedure, for example, about 24 hours after, or about 30 hours after.

In an exemplary embodiment of the invention, the pressure on the radial artery is controlled so that enough blood flows through the vessel to prevent or reduce the formation of a clot (e.g., occlusive clot). Potentially, radial artery occlusion is prevented by the selective application of pressure.

In an exemplary embodiment of the invention, the device comprises one or more sensors adapted to sense one or more parameters associated with blood flow through the radial artery. Optionally, the sensor is adapted to sense only blood flow through the radial artery, and not through other nearby vessels, for example, the sensor is small enough to sense only the artery. Optionally, the speed of blood flow through the radial artery is measured. Alternatively or additionally, the volume of blood flow through the radial artery is measured. Optionally or additionally, the sensor measures tissue oxygen content (e.g., tissue oximetry) distal to the compression site, for example, a pulse oximeter sensor is positioned on a finger (e.g., index finger).

In some embodiments, the sensor is Doppler sensor, for example, ultrasound and/or laser.

In an exemplary embodiment of the invention, the sensor is adapted to sense the direction of blood flow. Optionally, the sensor is adapted to distinguish between forward blood flow (e.g., coming from the heart, through the radial artery access site, and towards the hand) and reverse blood flow. Potentially, determining the direction of blood flow helps to distinguish between the desired blood flow through the radial artery access site and misleading reverse blood flow (e.g., from the ulnar artery).

In an exemplary embodiment of the invention, the sensor is positioned distal to the access site, but before the radial artery bifurcates and/or before the radial artery becomes one of the arterial arches of the hand. Alternatively or additionally, the sensor is positioned over the access site (e.g., the bleeding site) of the radial artery, in practice, along the wrist. Potentially, the positioning of the sensor provides a more accurate measure of blood flow through the accessed radial artery site, for example, preventing or significantly reducing measuring misleading collateral blood flow (e.g., from the ulnar artery).

In an exemplary embodiment, the pressure application is dynamically and automatically controlled. In some embodiments, the applied pressure is controlled according to one or more pressure protocols, for example, time dependent pressure, blood flow dependent pressure. Optionally, pressure on the radial artery access site is selectively increased. Alternatively, pressure on the radial access site is selectively decreased. Alternatively, pressure on the radial access site is maintained.

In an exemplary embodiment of the invention, pressure is adjusted so that blood flow is maintained within a predetermined range. Optionally, the predetermined range is determined according to a baseline. For example, calibration data obtained from experimental measurements of blood flow in the radial artery of sample patients. In another example, the range is determined according to initialization data obtained from the patient themselves (e.g., measurements before the procedure). For example, the blood volume flowing per unit time across the access site is maintained to be at least 20% of baseline, or at least 30%, or at least 50%, or other smaller, intermediate or larger values. In an exemplary embodiment of the invention, the blood flow is adjusted to the highest value within the range (e.g., relative to the baseline) without causing external bleeding.

Optionally, the applied pressure is strong enough to prevent pulses from being transmitted through the radial artery access site. Alternatively or additionally, the applied pressure is strong enough so that if the ulnar artery is occluded, the remaining blood flow through the radial artery is insufficient to adequately oxygenate the hand. Alternatively, the applied pressure is not strong enough to prevent pulses and/or is weak enough to allow enough blood to pass through to adequately oxygenate the hand (even if the ulnar artery is occluded).

In an exemplary embodiment of the invention, the pressure applied to the radial artery portion, is for example, about 60 mmHg to about 100 mmHg, or about 70 mmHg to about 90 mmHg, or about 75 mmHg to about 85 mmHg, or other smaller, intermediate or larger pressures are applied.

In an exemplary embodiment of the invention, the pressure applied to the radial artery portion reduces the blood flow through the radial artery portion, for example, to about 10 milliliters/minute to about 50 milliliters/minute, or about 20 ml/min to about 40 ml/min, or about 15 ml/min to about 35 ml/min, or other smaller, intermediate or larger values.

In an exemplary embodiment of the invention, the device is electrically coupled to a feedback unit. Optionally, the feedback provides an indication of the amount of blood flowing through the radial artery, for example, related to the protocol, threshold and/or range. Optionally or additionally, the feedback provides an indication of bleeding from the site. For example, the feedback comprises of a green light (e.g., indicating no bleeding and sufficient blood flow to reduce the risk of radial artery occlusion) or a red light (e.g., indicating bleeding, insufficient blood flow to reduce the risk of radial artery occlusion, or other problems).

An aspect of some embodiments of the invention relates to a device comprising a sensor adapted to sense a parameter associated with an amount of blood flow in a radial artery and to provide an output associated with varying levels of the blood flow. In an exemplary embodiment of the invention, the sensor is an ultrasound based Doppler sensor.

In some embodiments, the sensor is adapted to determine a direction of the blood flow, for example, to distinguish between forward and reverse blood flow through the radial artery.

In an exemplary embodiment of the invention, the sensor is sized and shaped for positioning on the skin overlaying the radial artery access site and/or downstream from the access site.

In some embodiments, the sensor is sized and shaped for use with other available radial artery closure devices, for example, the sensor is small and/or flat so that the radial closure device can be placed adjacent and/or overlaying the sensing device. One example of feedback of the measured blood flow and/or direction provided by the device uses different colored light emitting diodes (LEDs).

Potentially, the feedback from the sensor is used by a healthcare professional to manually adjust the pressure exerted by the available radial artery device, to stop bleeding while allowing sufficient blood to flow to reduce a radial artery occlusion risk.

An aspect of some embodiments of the invention relates to a method for stopping bleeding from a radial artery, the method comprising applying pressure to allowing blood to flow through the radial artery in an amount that prevents formation of a clot, the pressure being enough to stop bleeding, optionally monitoring the blood flow through the radial artery, and adjusting or maintaining the pressure according to the monitoring.

In an exemplary embodiment of the invention, the method comprises performing a calibration step. Optionally, a baseline measurement of the blood flow parameters is made. Optionally or additionally, one or more measurements correlating applied pressure to blood flow parameters are made.

In an exemplary embodiment of the invention, the pressure is applied according to a predefined protocol. Alternatively or additionally, the pressure is applied according to a predefined range and/or threshold. Optionally, the protocol defines the change (or maintenance) of the blood flow parameters over time. Alternatively or additionally, the protocol defines the change (or maintenance) of the applied pressure to the radial artery site over time.

In an exemplary embodiment of the invention, a predefined range and/or threshold is related to the baseline value. For example, the rate of blood flow is maintained to be at least about 30% of the baseline, or at least about 50%, or at least about 70%, or about 30%-70%, or about 20%-80%, or 50%-70%, or other smaller, intermediate or larger values. For example, the blood pressure is maintained below the diastolic peak blood pressure (e.g., as measured during baseline). For example, oxygenation of the hand is maintained (alone or together with other blood flow parameters) at 88% or greater, or 90% or greater, or 92% or greater, or 96% or greater, or other intermediate or larger values. For example, the radial artery is occluded to reduce the cross sectional area by about 50-90%, or by about 70-90%, or to about 2.0 mm diameter, or to about 1.5 mm, or to about 1.0 mm, or to about 0.5 mm, or other smaller, intermediate or larger percentages.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Overview

FIG. 1 is a schematic of a blood supply of a left hand 100, to help understand radial artery 102 access (e.g., for catheter based procedures), in accordance with an exemplary embodiment of the invention. Left hand 100 is shown palm up. Left hand 100 is used for illustration purposes only, as arterial access can also be obtained from the right hand.

Generally (a common anatomy will be described, although it should be understood that anatomical variations exist that can be utilized in accordance with an exemplary embodiment of the invention) blood flowing from the aorta reach the brachial artery, which branches into radial artery 102 and ulnar artery 104, which run along the sides of the wrist. In the hand, radial artery 102 and ulnar artery 104 meet (anastamose) into a superficial palmar arch 108 and a deep palmar arch 106, with branch vessels 110 supplying tissues of the hand.

Access to radial artery 102 can be obtained by cannulating artery 102, for example, in a region 112 about 2-3 cm above the crease of the wrist (exemplary region shown by dashed border), and introducing a needle 114 and/or guidewire 116 and/or sheath. The introduced tools can then be used to access targets within the vascular system, for example, to perform procedures in the heart such as deployment of stents in the coronary arteries.

Upon removal of the catheter from the radial artery, puncture 118 (or in some cases a laceration) requires closure before the patient is discharged home.

Exemplary Radial Artery Closure Device

Figure 2:
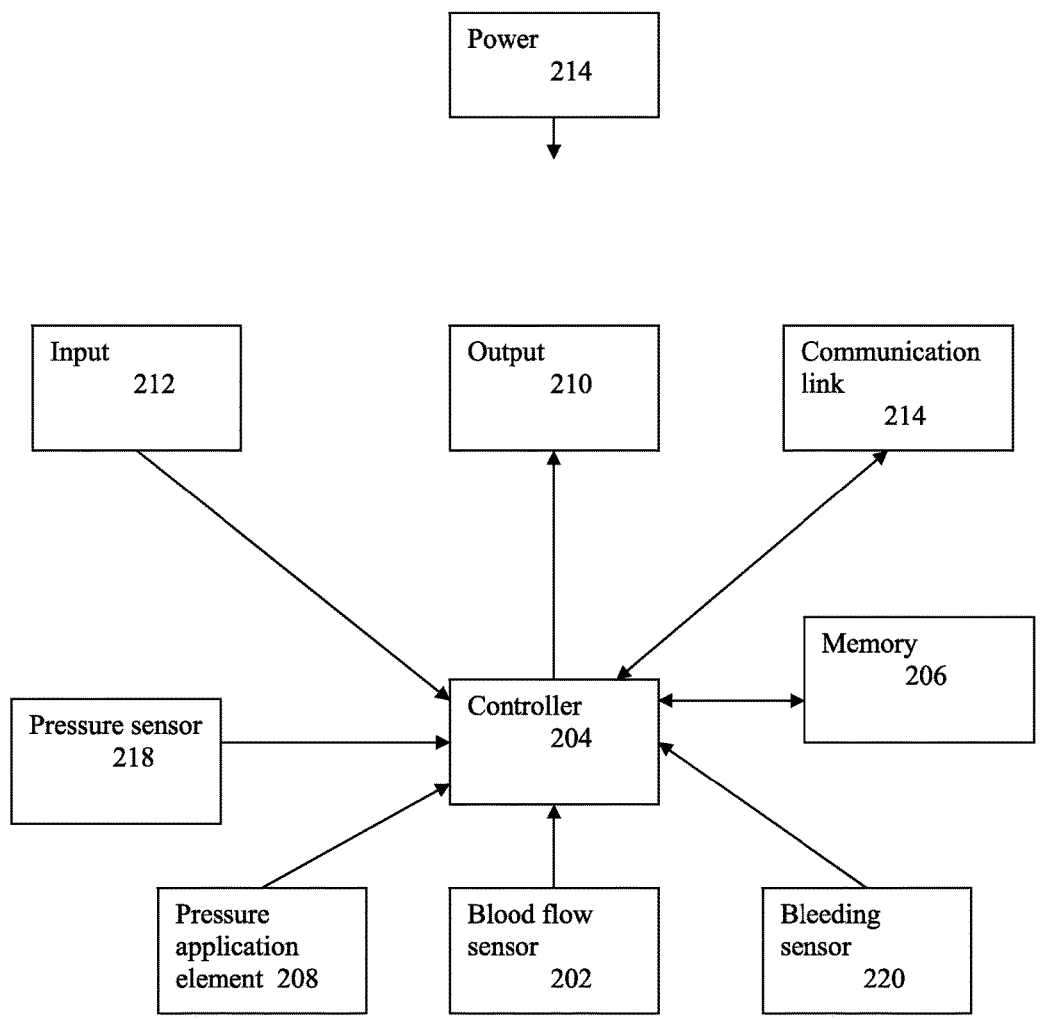
FIG. 2 is a block diagram of an exemplary radial artery closure device, in accordance with an exemplary embodiment of the invention.

FIG. 2 is a block diagram of an exemplary radial artery closure device 200, in accordance with an exemplary embodiment of the invention. In an exemplary embodiment of the invention, device 200 is adapted to monitor blood flow through the radial artery, and selectively apply pressure to the radial artery access site so that bleeding is prevented from the site while at least some blood continues to flow through the radial artery at the access site. In an exemplary embodiment of the invention, the pressure is controlled to allow enough blood to flow so that radial artery occlusion is reduced and/or prevented (e.g., by preventing formation of thrombus in the radial artery).

In an exemplary embodiment of the invention, device 200 comprises at least one blood flow sensor 202 that is adapted to sense one or more parameters associated with blood flow. Not necessarily limiting examples include: direction of blood flow, speed of blood flow (e.g., meters/second), rate of blood flow (liters/minute), blood pressure, pulsations, oxygen saturation level, peak systolic velocity, end-diastolic velocity, mean flow velocity, pulsatility index and resistance index.

In an exemplary embodiment of the invention, blood flow sensor 202 is an ultrasound based Doppler sensor. Alternatively or additionally, other sensors are used to measure one or more parameters of blood flow, not necessarily limiting examples include: an optical Doppler sensor, a photoplethysmograph, a sensor for impedance plethysmography, a sensor for magnetic flow measurement techniques.

In an exemplary embodiment of the invention, device 200 comprises one or more pressure application elements 208 adapted to apply a controlled pressure to a surface area. Optionally, pressure is applied to the skin area overlying the radial artery access site. Alternatively, pressure is applied directly to the radial artery itself, for example, through the skin puncture used to access the artery. Not necessarily limiting examples of pressure application elements 208 include; an inflatable enclosure, a piston.

In an exemplary embodiment of the invention, pressure application elements 208 are automatically controlled upon receiving of suitable signals. Alternatively or additionally, pressure application elements 208 are manually controlled, for example, a screw is used to manually adjust pressure exerted by a piston, or a valve is used to manually adjust pressure exerted by a pressurized bladder.

In some embodiments, device 200 comprises a pressure sensor 218 adapted to sense the applied pressure, for example, the pressure applied by pressure application element 208. Optionally, sensor 218 is adapted to generate a signal in response to the applied pressure. Optionally, sensor 218 is integrated with pressure application element 208, for example, located within pressure application element 208. Alternatively, sensor 218 is a separate component, for example, positioned between application element 208 and the skin surface.

In an exemplary embodiment of the invention, device 200 comprises a controller 204 adapted to control one or more elements of device 200. In an exemplary embodiment of the invention, controller 204 is in electrical communication with blood flow sensor 202, so that signals generated by sensor 202 are received by controller 204. Optionally, the blood flow signals are analyzed by controller 204. In an exemplary embodiment of the invention, controller 204 is in electrical communication with pressure application element 208, so that signals generated by controller 204 are sensed by elements 208. Optionally, elements 208 increase, decrease or maintain the applied pressure according to the signals. In some embodiments, controller 204 receives signals generated by pressure sensor 218. Optionally, the signals sent to pressure application element 208 are selected according to the measured pressure.

In an exemplary embodiment of the invention, controller 204 is an application specific integrated circuit (ASIC), for example, residing on a circuit board in device 200. Alternatively or additionally, controller 204 is a general purpose controller programmed with software. Alternatively or additionally, one or more functions of controller 204 are performed physically separated from the device, for example, signals can be transmitted to an externally located computer and/or smartphone, and/or signals can be transmitted to a remote server.

In some embodiments of the invention, controller 204 is in electrical communication with a memory 206 storing data. Optionally, memory 206 is adapted for writing thereto, in addition to being read from. In some embodiments, memory 206 stores instructions for operating controller 204. In some embodiments, memory 206 stores data collected from one or more sensors, for example, from blood flow sensor 202. In some embodiments, memory 206 stores correlation data, for example, changes in blood flow correlated with applied pressure. In some embodiments, memory 206 stores predefined protocols, for example, pressure protocols, blood flow control protocols.

In some embodiments, device 200 comprises one or more output elements 210 adapted to provide visual and/or auditory output. Optionally, output elements 210 are electrically coupled to one or more components of device 200, for example, controller 204 and/or blood flow sensor 202 so that signals provided by the components are sensed by output elements 210. Optionally, output elements 210 provide output corresponding to the sensed signals. Not necessarily limiting examples of output include; flashing lights, color coded lights, a screen for displaying numbers, a screen for displaying images, a speaker (e.g., to sound beeps, verbal messages, or other sounds).

In some embodiments, device 200 comprises one or more input elements 212 adapted to allow a user to select one or more options on device 200. Not necessarily limiting examples of input elements 212 include; switch (e.g., on/off), keypad, touchscreen, mouse, trackball, microphone (e.g., for voice recognition commands), buttons.

In some embodiments of the invention, device 200 comprises one or more communication elements 214 adapted to transmit signals to other devices in electrical communication with device 200. Optionally or additionally, communication elements 214 are adapted to receive signals. Not necessarily limiting examples of signals include; signals associated with the blood flow parameters, control signals to program the controller, data stored on memory. Not necessarily limiting examples of communication elements 214 include, for example; a wireless signal to a wireless network, a wired signal to an attached laptop. Optionally, the signal is received by a monitoring station (e.g., computer on the ward, remote server, smartphone). Potentially, healthcare workers can monitor the device while continuing to do other tasks.

In some embodiments, device 200 comprises one or more bleeding sensors 220 adapted to detect bleeding from the radial artery access site. Optionally, bleeding sensors 220 generate a signal in response to the measured bleeding (or lack of bleeding). Optionally, controller 204 is in electrical communication with bleeding sensor 220, to receive the signals. Not necessarily limiting examples of bleeding sensors 220 include; an optical sensor to detect changes in skin color due to bleeding, a conductivity sensor to detect changes in skin surface conductivity due to bleeding.

In an exemplary embodiment of the invention, device 200 comprises one or more power sources 224 to provide power for the components as described herein. Optionally, power source 224 is portable, for example, batteries. Alternatively or additionally, power source 224 is external, for example, a cable is plugged into a wall outlet.

In some embodiments of the invention, the closure device is used to provide closure for other arteries that may be at risk of chronic occlusion, for example, the brachial artery, the ulnar artery.

In some embodiments, the closure device is used to provide closure of arteries damaged due to trauma, for example, lacerations due to slashing of the radial and/or ulnar arteries during a suicide attempt. Potentially, the device helps prevent or reduce chronic vessel occlusion.

Exemplary Monitoring Device

Referring back to FIG. 2, in some embodiments, a radial artery monitoring device 250 is adapted to monitor the radial artery. Optionally, device 250 is unable to directly control the applied pressure to the radial artery, for example, device 250 does not comprise pressure application element 208. In some embodiments, the applied pressure is controlled by an external device (e.g., programmed by the healthcare worker), or manually (e.g., by the healthcare worker). Optionally, the monitoring of device 250 is used to help adjust the applied pressure by the external device or manually. For example, device 250 provides output of the blood flow and the healthcare worker adjusts the pressure manually. The pressure can be adjusted until the output changes, indicating that the blood flow is within the desired range.

In some embodiments, device 250 comprises of blood flow sensor 202 in electrical communication with controller 204 (and optionally with memory 206), and with output 210. Potentially, device 250 monitors blood flow in the radial artery, providing output according to the blood flow. Further details of some exemplary outputs are provided herein.

In some embodiments, device 250 comprises of additional monitoring functions, for example, measuring the applied pressure 208. Optionally, output 210 provides an indication if the applied pressure is too low (e.g., potential risk of bleeding) or too high (e.g., potential risk of occlusion of the vessel). Optionally, device 250 comprises bleeding sensor 220, potentially helping to detect vessel bleeding.

In some embodiments, device 250 comprises input element 212.

In some embodiments, device 250 comprise communication link 214.

In some embodiments, device 250 comprises power 224.

In some embodiments, the monitoring device is used to monitor the radial artery, for example, with an indwelling cannula (radial artery cannulation).

Some Potential Advantages

Closure of the radial artery access site is different than closure of other vascular access sites, for example, the femoral artery. Potentially, some embodiments of the radial artery closure device and/or the described methods provide advantages over using devices and/or methods designed for use to close other vascular access sites, for example, the femoral artery.

Occlusion of the radial artery, stopping or significantly preventing blood flow, can occur even with relatively small amounts of applied pressure. Without being bound to theory, this is due to the position of the radial artery, being very close to the skin, and against bone, which can also allow the patient to tolerate excessive pressure. Potentially, use of the device prevents or reduces occlusion of the artery, by controlling pressure within the narrow range required to regulate blood flow.

Potentially, radial artery occlusion complications are reduced and/or prevented.

Potentially, use of manual techniques to evaluate the status of the radial artery, for example, Barbeau's test, Allen's test, are not required.

Potentially, time to closure of the bleeding vessel is reduced, even in anticoagulated patients. Potentially, rebleeding is reduced and/or prevented. Generally, pressure is required to close the radial artery. For example, due to the small size of the artery and the small puncture forming the access site, closure devices (such as used in the femoral artery) are not available or not useful.

Potentially, patients otherwise excluded from transradial percutaneous procedures can now be treated with device monitoring.

Potentially, use of the device reduces errors in monitoring blood flow through the radial artery, for example, by incorrectly including collateral blood flow from the ulnar artery. For example, a pulse oximeter placed on a finger can show good oxygenation levels, even with an occluded radial artery (blood provided by the ulnar artery).

Exemplary Method of Operation

Figure 3:
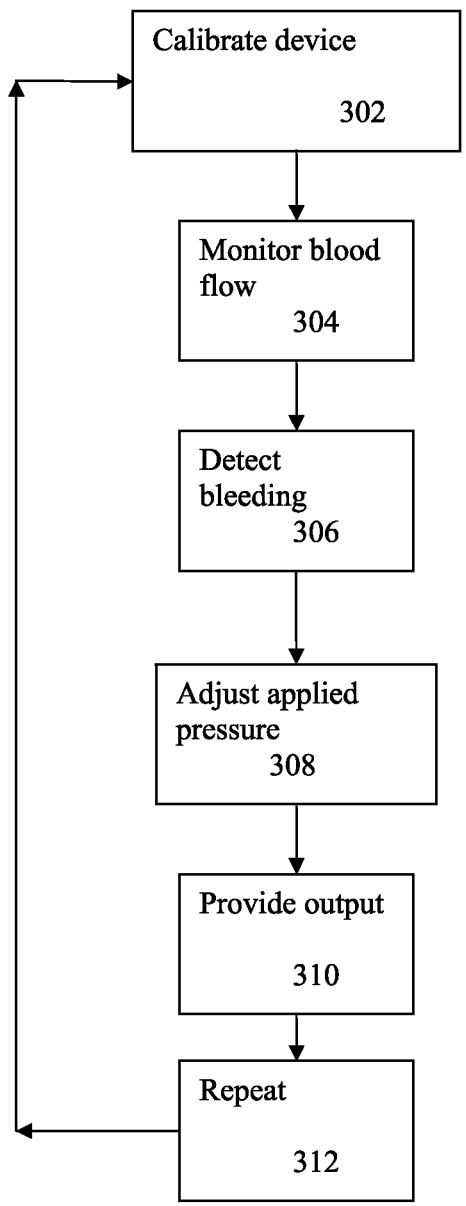
FIG. 3 is a flow chart of a method of operation of the radial artery device, in accordance with an exemplary embodiment of operation.

FIG. 3 is a flowchart of an exemplary method of operation of the radial artery access site closure device, in accordance with an exemplary embodiment of the invention. The method is not meant to be necessarily limited to the devices described herein, but other devices can also be used. The method is also not necessarily limited to the boxes described herein, as some boxes are optional and/or the order is optional.

Optionally, at 302, one or more calibration measurements are performed on the radial artery, for example, by the closure device. Optionally, the calibration data comprises of baseline data, for example, one or more parameters associated with blood flow through the radial artery access site. Alternatively or additionally, the calibration data comprises of associations between applied pressure to the access site and the resulting changes in one or more parameters of blood flow through the vessel.

Optionally, the calibration data is collected from the patient. Alternatively or additionally, the calibration data is collected from a group of subjects (patients and/or healthy). Alternatively or additionally, the calibration data is based on a mathematical model of the anatomy and/or physiology.

In some embodiments, calibration data is obtained before the procedure, before the access site has been formed by the physician. Alternatively or additionally, the calibration data is obtained after the access site has been formed (e.g., at the end of the procedure).

Optionally, the calibration data is collected by the device itself. In one example, the device is placed on the radial access site and placed into calibration mode (e.g., by pressing a button). In the example, the device performs one or more measurement of blood flow parameters, for example, by using the blood flow sensor. In the example, the device can perform additional measurements of blood flow as a function of applied pressure. For example, starting from no applied pressure, the device can incrementally (or continuously) increase pressure and measure the resulting changes in the blood flow parameter. Pressure can be increased until complete occlusion of the radial artery. The collected data can be stored as a table of the correlated values (e.g., on the memory), and/or a function can be calculated using the correlated data. Alternatively, pressure is first increased until occlusion (and/or until bleeding is stopped), and then incrementally decreased, for example, until bleeding resumes or until full patency (even if bleeding resumes).

In some embodiments, the calibration data is analyzed and/or processed to account for variability in the blood flow (e.g., due to systole/diastole, changes in cardiac output, effects of medications, changes in patient position). Optionally, a plurality of measurements are performed over time, for example, over several pulses. Optionally or additionally, the data is analyzed in various ways, for example, averaged, the distribution with standard deviation is calculated, minimum/maximum values are calculated.

In some embodiments, the calibration data is used to help define predetermined thresholds, ranges and/or protocols for the blood flow parameters. Optionally, the calibration data is used to help define thresholds, ranges and/or protocols for the applied pressure.

Optionally, the blood flow through the radial artery does not need to be large enough to adequately oxygenate and/or perfuse the hand (e.g., if the ulnar artery is occluded).

At 304, blood flow through the radial artery access site is monitored. In an exemplary embodiment of the invention, monitoring is performed by sensing one or more parameters associated with blood flow through the radial artery site. Optionally, the blood flow parameters are sensed by one or more sensors on the device, for example, the US Doppler sensor. Alternatively or additionally, the blood flow parameters are sensed by one or more sensors external to the device, for example, by a pulse oximeter with a sensor placed on the index finger of the hand having had the radial access.

In some embodiments, the monitoring is performed to account for variability. For example, repeated measurements over time that are averaged.

In an exemplary embodiment of the invention, the blood flow parameters are sensed just distally to the radial artery access site (e.g., downstream in the direction of blood flow). Optionally, the parameters are sensed proximal to a bifurcation of the radial artery (e.g., superficial palmar branch). For example, no more than about 3 mm away, or about 5 mm away, or about 10 mm away, or about 15 mm away, or about 20 mm away, or about 25 mm away, or other smaller, intermediate or larger distances. Alternatively or additionally, the blood flow parameters are sensed proximal to the radial artery access site. Alternatively or additionally, the blood flow parameters are sensed directly overlying the access site.

Potentially, at least some measurements of the blood parameters are performed without significantly measuring blood flow from the ulnar artery (e.g., through the superficial and/or deep palmar arches). Alternatively, at least some measurement of the blood parameters are performed including the blood flow from the ulnar artery, for example, to measure overall oxygenation of the hand.

Optionally, at 306, a bleeding state from the radial artery access site in determined, for example, automatically by the bleeding sensor and/or manually by the patient or by the healthcare provider. In some embodiments, the patient or the healthcare provider tell the device that bleeding has been detected, for example, by pressing a button on the device.

Optionally, bleeding is detected. Alternatively, bleeding is not detected. Alternatively, bleeding is suspected, for example, cannot be determined with reasonable accuracy.

At 308, the pressure being applied to the radial artery is adjusted. Optionally, the applied pressure is increased. Alternatively, the applied pressure is decreased. Alternatively, the applied pressure is maintained.

Optionally, the adjustment to the applied pressure is performed according to the monitored blood flow (e.g., as in 304). Optionally, the applied pressure is adjusted to try to change the blood flow parameter to fall within the range or the threshold. Alternatively or additionally, the applied pressure is adjusted to try to change the blood flow parameter according to a predefined protocol.

In some embodiments, the adjustment to the applied pressure is performed according to the table of values and/or function relating the blood flow parameter to the applied pressure. For example, upon measuring the blood flow parameter, if the parameter is outside the predefined range, the applied pressure is adjusted to the value in the table, to try to place the blood flow parameter within the predefined range.

In some embodiments, the adjustment to the applied pressure is performed without using correlation data (e.g., the table and/or function). In some embodiments, the adjustment is performed incrementally (e.g., by a predefined amount) or continuously (e.g., at a predefined rate) until the predetermined blood flow threshold is reached. For example, if the blood flow is too slow, the pressure is gradually reduced until the measured blood flow falls within a predefined range. For example, if the blood flow is too fast, the pressure is increased until the measured blood flow falls within the predefined range. For example, if blood flow is within the predefined range, the pressure is maintained.

Potentially, the adjustments help to compensate for unwanted changes in pressure and/or blood flow. For example, the radial artery can spasm, potentially reducing the blood flow therethrough, in which case the pressure can be reduced. For example, the pressurized air bag (e.g., pressure application element) can leak some air, requiring an increase in pressure.

Optionally, at 310, the device produces one or more outputs. Optionally, the outputs are used to provide feedback on what the device is doing, but do not require any action. Alternatively, the outputs are used to alert the user and/or healthcare workers that some action is required.

In some embodiments, the device provides an alert if bleeding is detected.

In some embodiments, the device provides an alert if the blood flow parameter does not fall within the pre-specified range or threshold and/or protocol.

In some embodiments, the device tries to resolve the problem before sounding the alarm, for example, by trying to adjust the applied pressure.

Optionally, at 312, one or more of 304, 306 and/or 308 are repeated. For example, the monitoring and/or adjustments are performed 10 times per second, once per second, once per 5 seconds, once per 10 seconds, once per 30 seconds, once per minute, once per 5 minutes, once per 10 minutes, or other smaller, intermediate or larger time frames are used.

In some embodiments, the method is used with the radial artery monitoring device (e.g., device 250 of FIG. 2). Optionally, some boxes are performed in a different order. For example:

Optionally, at 302, the monitoring device is calibrated, for example, as described herein.

At 304, the monitoring device monitors parameters of blood flow, for example, as described herein.

In some embodiments, the monitoring device monitors the applied pressure (e.g., exerted by the external device and/or manually).

Optionally, at 306, the monitoring device detects bleeding from the radial artery, for example, as described herein.

At 310, the monitoring device provides output. Optionally, the output is related to the sensed blood flow parameters, for example, according to absolute values, to thresholds, ranges and/or protocols. Optionally or additionally, the output is the state of bleeding or lack of bleeding or suspected bleeding. Optionally or additionally, the output is related to the amount of applied pressure.

In some embodiments, the output consists of instructions to the user, for example, to increase the applied pressure or to decrease the applied pressure.

Optionally, at 308, the applied pressure is adjusted. Optionally, the adjustment is performed manually, for example, by the healthcare worker adjusting the pressure exerted by the external device. Optionally, the adjustment is performed according to the output as in 310.

Optionally, at 312, one or more of 302, 304, 306, 308, and/or 310 are repeated, for example, as described herein.

In some embodiments, some steps are optional. For example: In some embodiments, the calibration (e.g., 302) is not performed. Optionally, the blood flow is controlled to be within the predetermined threshold and/or according to the protocol without the calibration.

In some embodiments, the blood flow is not monitored (e.g., as in 304). Optionally, the pressure is adjusted and/or maintained according to a preselected threshold or range and/or pressure protocol. For example, the pressure is monitored to detect if the applied pressure is within the range (e.g., by the pressure sensor). The applied pressure is adjusted to be within the range. In another example, the applied pressure is maintained or adjusted without any monitoring, for example, according to a preselected protocol.

In some embodiments, bleeding detection (e.g., as in 306) is not performed. Optionally, the applied pressure is selected to be sufficiently high to reduce the risk of bleeding.

Exemplary Design of the Radial Artery Closure Device

Figure 4:
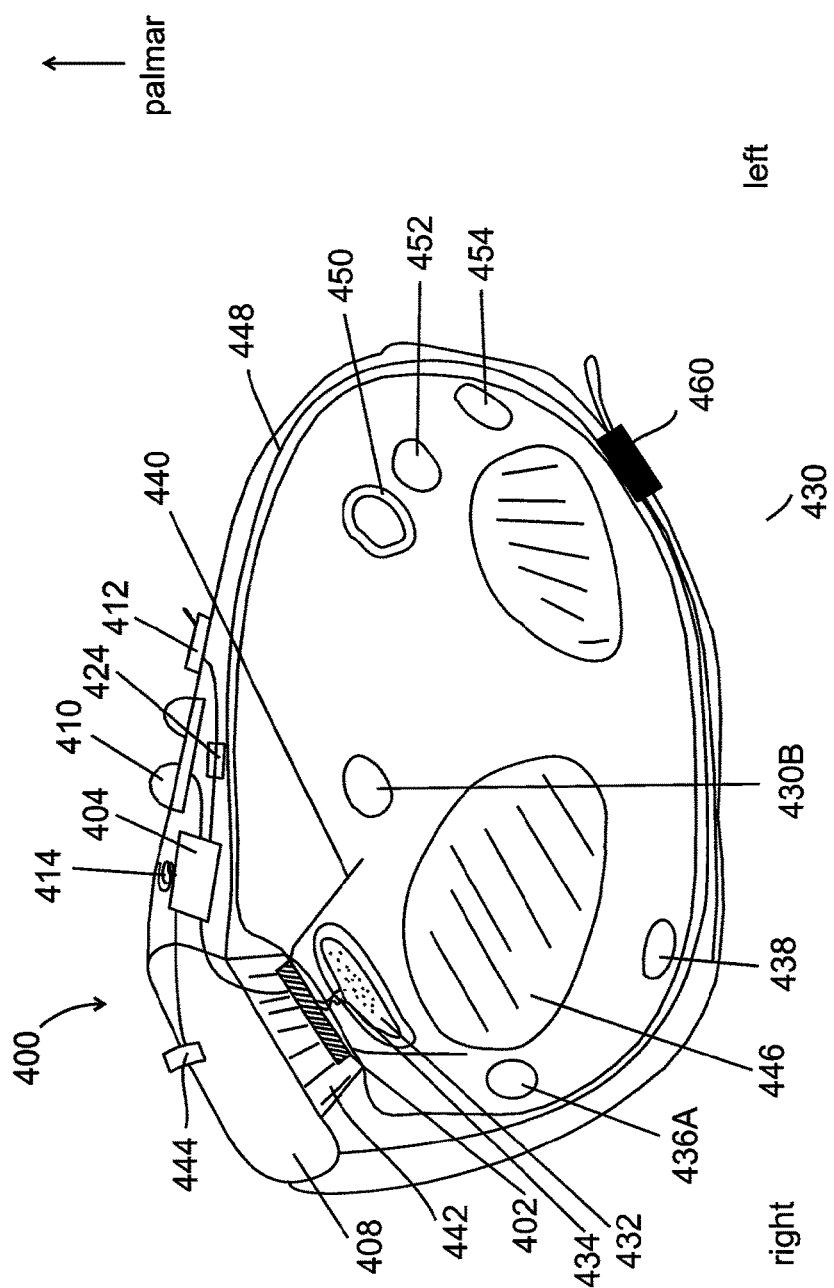
FIG. 4 is a simplified diagram of an exemplary design of the radial artery closure device, in accordance with an exemplary embodiment of the invention.

FIG. 4 is a schematic of an exemplary design of a radial artery closure device 400, in accordance with an exemplary embodiment of the invention. Device 400 monitors blood flow parameters of the radial artery, and selectively applies pressure to the artery to prevent bleeding and allow enough blood flow to prevent or reduce radial artery occlusion.

FIG. 4 is a cross section through a right wrist 430 (palm up), with device 400 positioned to monitor and/or apply pressure to a radial artery 432. For illustrative purposes, artery 432 is shown as being partially compressed, with the compression sufficient to prevent bleeding from access site 434, and the compression not being sufficient to fully occlude the lumen of artery 432. In an exemplary embodiment of the invention, at least some blood continues to flow (e.g., in the direction from the heart to the hand) through the lumen, the pressure is controlled so that blood flows within one or more preset ranges or thresholds. Optionally, the compression is insufficient to clinically affect nearby nerves (e.g., radial nerve 436A. median nerve 436B), for example, causing numbness and/or tingling. Optionally or additionally, the compression is insufficient to clinically affect nearby veins (e.g., cephalic vein 438), for example, causing engorgement. Without being bound to theory, artery 432 is easily compressible against radius bone 446 with relatively low amount of force.

In an exemplary embodiment of the invention, a blood monitoring sensor, for example, Doppler sensor 402 is positioned so that US beam 440 scans a cross section of radial artery 432. Optionally, sensor 402 is positioned over access site 434. Alternatively, sensor 402 is positioned downstream from access site 434.

In an exemplary embodiment of the invention, Doppler sensor 402 is adapted for transmitting an imaging US beam 440, for example, a low power beam. Optionally, no special settings are required.

In an exemplary embodiment of the invention, sensor settings (e.g., the frequency and/or intensity) are selected so that the sensor can sense one or more parameters associated with blood flow through the radial artery portion across the tissues between the radial artery and the skin. Optionally, the beam does not need to penetrate further than the bone underneath the radial artery (radius). The sensor is adapted to sense at a depth of no more that about 1 mm, or no more than about 3 mm, or no more than about 5 mm, or no more than about 7 mm, or no more than about 10 mm, or no more than about 15 mm, or other smaller, intermediate or larger distances.

Optionally, Doppler sensor 402 has a surface area large enough to scan a cross section of artery 432. For example, measuring: about 5 mm×5 mm, or about 10 mm×3 mm, or about 10 mm×10 mm, or about 15 mm×15 mm, or about 20 mm×20 mm, or about 10 mm×5 mm, or about 25 mm$^2$ to about 400 mm$^2$, or about 50 mm$^2$ to about 200 mm$^2$, or about 25 mm$^2$ to about 100 mm$^2$, or other smaller, intermediate or larger values.

In some embodiments, Doppler sensor 402 is integrated within a pressure application element, for example, a rigid element (e.g., made from plastic) 442 adapted to apply pressure to a surface area of skin.

In some embodiments, rigid element 442 has a surface area larger enough to compress radial artery 432. Optionally, the surface area is not large enough to compress surrounding structures (e.g., to a clinically significance compression). The area of rigid element 442 is, for example, about 5 mm×5 mm, or about 10 mm×5 mm, or about 20 mm×10 mm, or about 15 mm×10 mm, or about 15 mm×15 mm, or about 20 mm×20 mm, or about 25 mm$^2$ to about 400 mm$^2$, or about 50 mm$^2$ to about 200 mm$^2$, or about 25 mm$^2$ to about 100 mm$^2$, or other smaller, intermediate or larger areas.

In some embodiments, an expandable pressure container 408 is adapted to selectively apply force rigid element 442 towards the skin. Optionally, controlling the pressure inside container 408 controls the applied pressure on artery 432. Optionally, a pump 444 controls the air pressure inside container 408 (e.g., letting air in or out). Optionally, pump 444 is automatically controlled.

In some embodiments, controller 404 receives signals from US sensor 402. Optionally, controller 404 automatically analysis the sensed signals to estimate blood flow parameters. Alternatively or additionally, controller 404 processes the signals and displays Doppler images and/or sound for manual measurements and/or automatic analysis by other software. In some embodiments, controller 404 sends control signals to pump 444 to increase or decrease the pressure within container 408.

In some embodiments, device 430 comprises of other optional elements. Optionally, a communication element, for example, antenna 414 provides wireless transmission and/or receiver capabilities. Optionally or additionally, an output element, for example, color coded LEDs 410 provide visual output, for example, indicating if the blood flow is within the desirable range (e.g., green) or not (e.g., red). Optionally or additionally, an input element, for example, switch 412 allows the selection of different modes of operation (e.g., calibration, steady state, on/off). Optionally or additionally, a bleeding sensor, for example, a color sensor helps to detect bleeding from access site 434.

In an exemplary embodiment, a strap 448 is used to secure device 430 in position. Optionally, strap 448 is sized to fit around a wrist. Optionally, strap 448 does not exert pressure on other anatomical structures to a clinically significant degree. For example, ulnar artery 450 provides enough blood to the hand, ulnar nerve 452 does not produce symptoms and/or basilic vein 454 does not cause engorgement. Optionally, strap 448 is made out of a transparent material, potentially allowing visual detection of bleeding.

In some embodiments, strap 448 is secured in position using a clasp 460 or other methods, for example, velcro. Optionally, strap 448 is inelastic. Potentially, the inelastic strap helps to improve control of the pressure applied to the radial artery. Alternatively, the strap is selectively elastic, for example, to prevent overly applying pressure to the radial artery. In some embodiments, the elastic strap does not include the clasp.

Exemplary Design of the Monitoring Device

Figure 5:
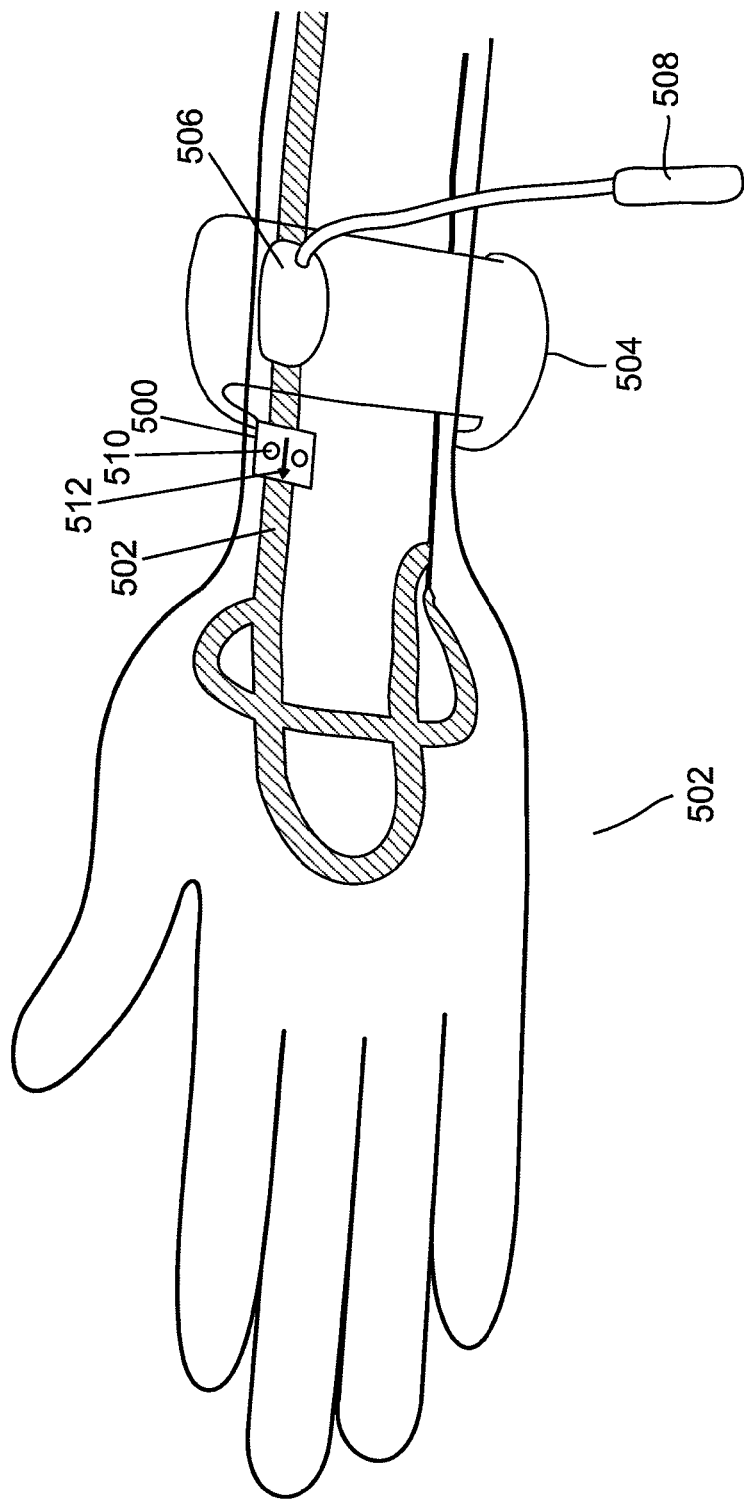
FIG. 5 is a simplified diagram of an exemplary design of the radial artery monitoring device, in accordance with an exemplary embodiment of the invention.

FIG. 5 is a schematic of an exemplary design of a radial artery monitoring device 500, in accordance with an exemplary embodiment of the invention. Device 500 is shown as being positioned on a right hand 502 (including the wrist). For clarity, major blood vessels of the wrist and hand are illustrated. In an exemplary embodiment of the invention, device 500 monitors a radial artery 502 for one or more parameters associated with blood flow.

In an exemplary embodiment of the invention, device 500 is used as an add-on to existing closure devices.

In an exemplary embodiment, device 500 comprises a blood flow control sensor, for example, a US Doppler sensor.

In some embodiments, device 500 comprises one or more output elements, for example, color coded light emitting diodes 510. Optionally, device 500 comprises a controller adapted to control the lights according to the sensed blood flow parameters. For example, if one or more sensed parameters fall within the desired range or threshold, a green light is turned on. For example, if one or more sensed parameters are below the threshold or outside the range, a red light is turned on.

In an exemplary embodiment of the invention, device 500 integrates components into a small area, for example, about 10 mm×10 mm, or about 15 mm×10 mm, or about 20 mm×20 mm, or other smaller, intermediate or larger areas. Other components of device 500 are described, for example, with reference to FIG. 2.

In an exemplary embodiment of the invention, device 500 is used with an external radial artery application device 504, for example, integrated with, or sold separately. Any suitable device 504 can be used, for example, commercially available devices such as the Terumo TR Band™, HemoBand®. Optionally, device 504 comprises of a pressure application element, for example, a flexible reservoir 506 that is adapted to be filled with air. Optionally, the air pressure in reservoir 506 is controllable, for example, by insertion or removal of air through a valve 508. Optionally, pressure applied to radial artery 502 is controllable by regulation of the air pressure inside reservoir 506, for example, manually by a healthcare provider, according to the output provided by device 500.

In some embodiments, the source of gas is integrated into the wrist band (e.g., external device 504). Optionally, valve 508 is integrated into the wrist band, not requiring additional tubing. Alternatively or additionally, a pressurized gas source is integrated into the wrist band, for example, a small gas canister, a battery operated micro-pump.

In some embodiments, gas is selectively moved between two or more chambers to control the applied pressure. Optionally, the chambers are in fluid communication with each other. Optionally, changes in gas pressure and/or volume of one or more chambers affect the pressure being applied to the radial artery (e.g., by direct contact of the chamber with the skin, or indirectly by urging a resilient element against the skin), for example, reservoir 506. Optionally or additionally, changes in gas volume and/or pressure in one or more different chambers do not affect the force of the pressure being applied to the radial artery. For example, the chambers expand towards the air, or the chambers do not expand. In some embodiments, the force applied to the radial artery is controlled by movement of gas/air between the non-pressure applying chamber and the pressure applying chamber. For example, movement of gas into the pressure chamber from the non-pressure chamber increases the force of the pressure applied to the radial artery. For example, movement of gas from the pressure chamber to the non-pressure chamber reduces the pressure applied to the radial artery. The air movement is controlled, for example, by a battery operated micropump.

Optionally, the volumes of the pressure applying chambers and the non-pressure applying chambers are about equal. Alternatively, the volume of the non-pressure applying chamber is larger than the pressure applying chamber, for example, about 20% greater, or about 50%, or about 100% greater, or other smaller, intermediate or larger values. Potentially, the relative volume between the chambers is selected to help improve control of the applied pressure.

In some embodiments, device 500 is marked with a mark 512 to help the user position device 500 correctly, for example, so that blood flow direction can be evaluated. Not necessarily limiting examples of marks 512 include; an arrow pointing in the direction of blood flow, an 'X' positioned on the downstream direction, color codes.

In some embodiments, device 500 is secured to the skin with an adhesive, for example, a biocompatible glue couples device 500 to the skin. Optionally, device 500 is sold with the adhesive already disposed on the contact surface, for example, the user removes a disposable cover to expose the adhesive, and then attaches device 500 to the skin using the adhesive. Alternatively or additionally, tape is used to secure device 500 to the skin.

In some embodiments, device 500 is placed downstream of external device 504. Alternatively, external device 504 is positioned to overlap device 500, for example, air reservoir 506 is positioned overtop of device 500.

Exemplary Method of Treatment

Figure 6:
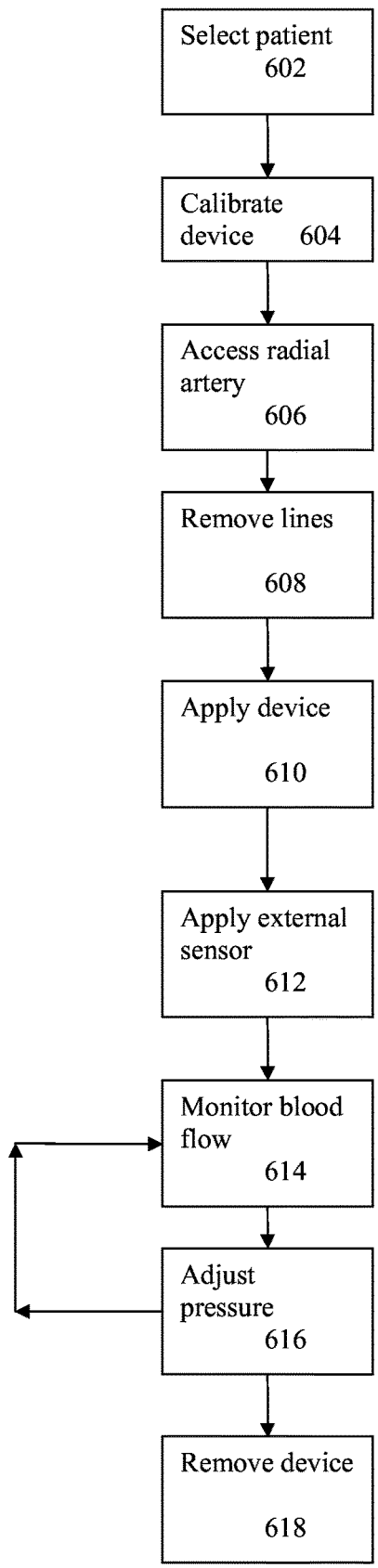
FIG. 6 is a flowchart of a method of treatment, in accordance with an exemplary embodiment of the invention.

FIG. 6 is a method of treatment using the radial artery closure device and/or the monitoring device, in accordance with an exemplary embodiment of the invention. The method is not limited to the described devices herein, as other devices can also be used. Furthermore, the method as described is not necessarily limiting, as some boxes are optional, and some boxes can be performed in different orders.

Optionally, at 602, a patient is selected for radial artery closure using the device. For example, the physician does the selecting. In one example, patients are excluded from radial artery access based on one or more exclusion criteria; known upper extremity vascular disease, severe Raynaud's, abnormal Allen's test.

Optionally, at 604, the device is calibrated on the radial artery before the artery is accessed. Alternatively or additionally, the device is provided pre-set, for example, with the desirable ranges and/or thresholds and/or protocols.

Optionally, at 606, the radial artery is accessed, for example, 2-3 cm above the crease of the wrist. Optionally, the patient is treated with an anticoagulant to help prevent formation of thrombus in the radial artery. For example, 5000-10000 units of Heparin administered intra-arterially.

Optionally, at 608, the procedure is ended and the indwelling lines are removed from the radial artery.

At 610, the radial artery closure device is applied to the radial artery access site. Optionally, an acoustic coupling gel is applied between the skin and the US element. Optionally, the device is activated, for example, by pressing a switch.

Alternatively, in some embodiments, the radial artery monitoring device is applied to monitor blood flow through the radial artery. Optionally, an external closure device is applied to the radial artery access site.

In some embodiments, pressure is first applied to stop bleeding, before any monitoring of blood flow starts. Optionally, pressure is manually applied, for example, by the physician. The physician can apply pressure using standard techniques (e.g., absorbable pad), using the existing device (e.g., manually inflating the pressure application pillow), or using other available devices. Alternatively, pressure is automatically applied by the device. For example, the device increases pressure until total vessel occlusion to ensure bleeding is stopped, before trying to control blood flow through the site.

Optionally, at 612, one or more external sensors are applied to monitor the patient. Optionally, a pulse oximeter is applied to the finger of the patient, for example, to monitor the overall oxygenation of the hand.

At 614, the blood flow through the radial artery is monitored. Optionally, monitoring is performed to determine if the blood flow falls within predefined thresholds and/or ranges. Optionally or additionally, bleeding is monitored.

In some embodiments, the device alerts the healthcare provider as to the status of the blood flow and/or bleeding, for example, by an alarm.

At 616, the blood flow through the radial artery is adjusted. Alternatively, blood flow is maintained. In some embodiments, the adjustment is performed by changing or maintaining the pressure applied to the artery.

In some embodiments, the adjustment is performed automatically by the device. Alternatively, the heatlthcare provider manually adjusts the pressure, for example, based on feedback from the device (e.g., as in 614).

In some embodiments, the monitoring (e.g., 614) and adjustment (e.g., 616) are repeatedly performed.

Optionally, at 618, radial site access closure has been determined, for example, by the physician. Optionally, the patient is discharged home.

In some embodiments, the radial device is disposable.

General

It is expected that during the life of a patent maturing from this application many relevant radial artery devices will be developed and the scope of the term radial artery device is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A vessel pressure control device configured for selectively applying pressure to a radial artery, said device comprising:
   a sensor configured to sense one or more parameters associated with blood flow through a portion of said radial artery;
   a rigid pressure application element adapted to apply variable amounts of pressure to said portion of said radial artery, wherein said sensor is integrated within said rigid pressure application element;
   an expandable pressure container adapted to apply force to said rigid pressure application element towards said portion of said radial artery; and
   a controller configured to apply logic and generate a signal to control said expandable pressure container in response to said one or more measured parameters, said signal controlling said expandable pressure container to modify or maintain said applied pressure so that at least some blood flow is maintained through said radial artery portion in an amount sufficient to reduce or prevent radial artery occlusion, and so that said applied pressure is sufficient to prevent bleeding from said portion.

2. A device according to claim 1, wherein said sensor comprises an ultrasound sensor positioned and adapted to measure a blood flow rate through said radial artery portion.

3. A device according to claim 1, wherein said sensor is adapted to sense said one or more parameters on a finger.

4. A device according to claim 1, further comprising a memory in electrical communication with said controller, said memory storing one or more value thresholds and/or ranges for monitoring said sensed parameter.

5. A device according to claim 1, further comprising a memory in electrical communication with said controller, said memory storing data associating said one or more parameters with an applied pressure.

6. A device according to claim 1, further comprising a wireless transmitter adapted to transmit signals associated with said one or more parameters.

7. A device according to claim 1, further comprising a bleeding sensor adapted to detect bleeding from said radial artery portion and send a bleeding signal associated with said bleeding to said controller, said controller adapted to send said signal to said expandable pressure container increase said applied pressure in response to said bleeding signal.

8. A device according to claim 1, further comprising an output element adapted to provide output associated with said one or more parameters.

9. A device according to claim 1, wherein said sensor is positioned within said rigid pressure application element.

10. A device according to claim 1, wherein said sensor is adapted to measure a direction of blood flow through said radial artery portion.

11. A device according to claim 1, wherein said rigid pressure application element has a pressure applying surface of about 25 $mm^2$ to about 400 $mm^2$.

12. A device according to claim 1, further comprising a strap sized to fit around a wrist.

13. A device according to claim 1, wherein said sensor is adapted to sense said one or more parameters at a depth of no more than about 10 mm.

* * * * *